United States Patent [19]

Abou-Gharbia et al.

[11] Patent Number: 4,957,909
[45] Date of Patent: Sep. 18, 1990

[54] BENZOBICYCLOALKANE DERIVATIVES AS ANTICONVULSANT NEUROPROTECTIVE AGENTS

[75] Inventors: Magid A. Abou-Gharbia, Glen Mills, Pa.; Ronald R. Notvest, Jamesburg, N.J.

[73] Assignee: American Home Products Corporation, New York, N.Y.

[21] Appl. No.: 459,874

[22] Filed: Jan. 2, 1990

Related U.S. Application Data

[62] Division of Ser. No. 347,538, May 4, 1989, Pat. No. 4,924,008.

[51] Int. Cl.$^5$ .............................................. A61K 31/66
[52] U.S. Cl. ...................................................... 514/75
[58] Field of Search .......................................... 514/75

[56]  References Cited

U.S. PATENT DOCUMENTS 4,001,331  1/1977  Freed et al. ...................... 260/571

OTHER PUBLICATIONS

J. Med. Chem. 16, 595 (1973).
J. Med. Chem., 19, 476 (1976).
J. Med. Chem., 19, 560 (1976).

Primary Examiner—Stanley J. Friedman
Attorney, Agent, or Firm—Richard K. Jackson

[57] ABSTRACT

The use of the compounds:

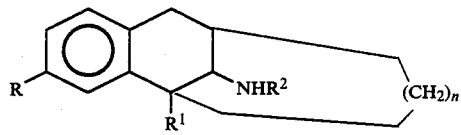

where R is hydrogen, alkyl, alkoxy, hydroxy, alkanoyloxy, phenylalkoxy, halo or trifluoromethyl; $R^1$ is alkyl, alkenyl or phenylalkyl; $R^2$ is hydrogen, alkyl, phenylalkyl, alkenyl, alkynyl, thienylalkyl or furylalkyl; n is one of the integers 2, 3, 4, 5 or 6; or a pharmaceutically acceptable salt thereof, as NMDA antagonists in the treatment of convulsions and neurodegenerative disease states. The compounds in which $R^2$ are heterocyclylalkylamines are novel and useful NMDA antagonists.

7 Claims, No Drawings

BENZOBICYCLOALKANE DERIVATIVES AS ANTICONVULSANT NEUROPROTECTIVE AGENTS

This is a division of application Ser. No. 07/347,538 filed May 4, 1989 now U.S. Pat. No. 4,924,008.

BACKGROUND OF THE INVENTION

Under physiological conditions, the excitatory amino acids, glutamic and aspartic acid, have an important role as excitatory neurotransmitters. It has been proposed that under certain pathological conditions, there is an excess release of excitatory amino acids which can cause overstimulation of the neurons. Such overstimulation by excitatory amino acids can cause convulsions, behavioral impairments and neuronal loss.

It has been proposed that the neurotoxic effects of excitatory amino acids may have a role in human neurodegenerative diseases such as Parkinson's disease, Pick's disease, Alzheimer's disease, Huntington's chorea, as well as other dysfunctions which occur in ischemia, epilepsy, stroke, and brain and spinal cord trauma or injury.

The excitatory amino acids are known to bind and activate several receptor complexes, including the N-methyl-D-asparatate (NMDA) receptor. NMDA itself can overstimulate neurons and produce convulsions and neuronal loss in animals. Thus, agents which antagonize NMDA can provide neuroprotection in conditions in which excess release of excitatory amino acids occurs.

DESCRIPTION OF THE INVENTION

It has been discovered that a portion of the group of known analgesic, anti-inflammatory agents disclosed by Freed et al. in U.S. Pat. No. 4,001,331 and certain novel N-heterocyclylalkyl analogues are non-competitive NMDA-antagonists useful as anticonvulsants and as neuroprotectants for avoidance of neurodegenerative diseases.

The compounds previously disclosed by Freed et al. which are useful in the process of this invention, are those embraced by the structural formula:

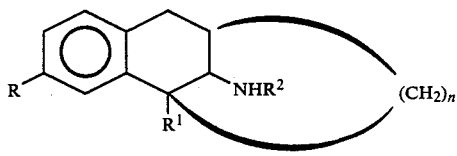

where
  R is hydrogen, alkyl of 1 to 6 carbon atoms, alkoxy of 1 to 6 carbon atoms, hydroxy, alkanoyloxy of 2 to 6 carbon atoms, phenylalkoxy having 1 to 6 carbon atoms in the alkoxy moiety, halo or trifluoromethyl;
  $R^1$ is alkyl of 1 to 6 carbon atoms, alkenyl of 2 to 6 carbon atoms or phenylalkyl having 1 to 6 carbon atoms in the alkyl moiety;
  $R^2$ is hydrogen, alkyl of 1 to 6 carbon atoms, phenylalkyl having 1 to 6 carbon atoms in the alkyl moiety, alkenyl of 2 to 6 carbon atoms, alkynyl of 2 to 6 carbon atoms;
and
  n is one of the integers 2,3,4,5 or 6;
or a pharmaceutically acceptable salt thereof.

Applicant's have also found that certain novel compounds of the above description in which $R^2$ is thienylalkyl having 1 to 6 carbon atoms in the alkyl moiety or furylalkyl having 1 to 6 carbon atoms in the alkyl moiety, as represented by the 2-furylmethyl species are similarly possessed of NMDA antagonist properties which characterizes them as anticonvulsant and neuroprotective agents.

Of the compounds described in the preceding paragraph, the preferred variables are those in which R is hydroxy, $R^1$ is methyl, $R^2$ is methyl and n is five.

The pharmaceutically acceptable salts contemplated in conjunction with the compounds useful in this invention are those non-toxic salts derived from either organic or inorganic acids such as hydrochloric, hydrobromic, sulfuric, phosphoric, methansulfonic, nitric, p-toluenesulfonic, citric, maleic, fumaric, malonic acids and the like.

The novel compounds of this invention containing an aromatic heterocyclylalkyl group as $R^2$ are prepared by reaction of the appropriate aromatic heterocyclicalkylaldehyde with the tricyclic amine to obtain a Schiff's base which is reduced in situ with zinc modified cyanoborohydride reagent in a suitable solvent such as methanol, thusly,

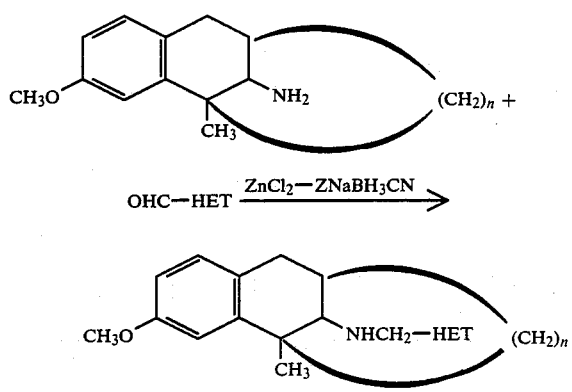

where HET represents an aromatic or pseudoaromatic heterocyclic ring such as furan, pyran, pyridine, pyrimidine, pyrazine, and the like.

The specific preparation of heterocyclylalkylamine derivatives of this invention is illustrated with 2-furylaldehyde as follows:

To a stirred solution of 13-amino-5,6,7,8,9,10,11,12-octahydro-3-methoxy-5-methyl-5,11-methanobenzocyclodecene (2.5 g, 0.0096 mol) in methanol (22 mL), was added 2-furylaldehyde (0.80 mL; 0.93 g; 0.0097 mol) and zinc modified cyanoborohydride (Kim et al., J. Org. Chem., 1985, 50, 1927) (0.5M in CH$_3$OH, 0.02 g, 0.01 mol) and the reaction mixture was stirred at room temperature overnight. To the stirred solution, 15 mL of 1M sodium hydroxide was added and the methanol was removed by evaporation under reduced pressure. The residue was partitioned in methylene chloride and water. Concentrated ammonium hydroxide was added until a clear solution was obtained. The methylene chloride layer was separated, dried and evaporated under reduced pressure to afford the crude N-(5,6,7,8,9,10,11,12-octahydro-3-methoxy-5-methyl-5,11-methanobenzocyclodecen-13-yl)-2-furanmethanamine which was purified by high pressure liquid chromatography and converted to the hydrochloride salt to afford 2.7 g (7.7% yield) of white solid; mp 231°-238° C.

Elemental analysis for $C_{22}H_{29}NO_2 \cdot HCl$; Calc'd: C, 70.31; H, 7.99; N, 3.73; Found: C, 70.09; H, 8.14; N, 4.55.

N-(5,6,7,8,9,10,11,12-octahydro-3-methoxy-5-methyl-5,11-methanobenzocyclodecen-13-yl)-2-thiophenemethanamine is produced by following the procedure of the preceding paragraph with the exception that 2-thiophenaldehyde is substituted for 2-furylaldehyde.

The anticonvulsion properties of these compounds was directly established by demonstrating the NMDA antagonist properties of representative compounds in male Swiss-albino mice (CD-1 strain, Charles River) 18–22 grams in weight after 18 hours of food deprivation which had been habituated to an observation chamber for 30 minutes. The mice were pretreated with the representative test compounds followed thirty minutes later with NMDA (195 mg/kg, i.p., the ED90 dose for generalized myoclonus). The mice were then observed for 30 minutes, noting the latency of onset of generalized myoclonus (uncontrollable hind leg scratching or limbs and/or torso muscle jerking with loss of righting reflex) and death. From the latter, the $ED_{50}$ for survival is determined. In this standard experimental test procedure, the specific compounds tested, which representatively establish the anticonvulsant activity for all the compounds herein, were (−)-13β-amino5α-methyl-5,6,7,8,9,10,11,12-octahydro-5,11-methano-benzocyclodecen-3-ol which was active as an anticonvulsant at from 1 to 100 mg/kg, i.p. and (−)-13β-methylamino-3-methoxy-5α-methyl-5,6,7,8,9,10,11,12-octahydro-5,11-methanobenzocyclodecene which exhibited an $ED_{50}$ for survival of 56 mg/kg, i.p. and 97 mg/kg, p.o. Thus, these NMDA antagonists are useful anticonvulsants.

In addition, the compounds involved herein were established as inhibitors of NMDA-induced neuronal release of norepinephrine by showing that (−)-13β-methylamino-3-methoxy-5α-methyl-5,6,7,8,9,10,11,12-octahydro-5,11-meth-anobenzocyclodecene inhibits 89 percent of the NMDA-induced norepinephrine release at 100 μM concentration in the following standard test procedure:

Rat hippocampal slices (0.5 mm thick) were incubated (37° C.) for 30 minutes in oxygenated (bubbled 95% $O_2$/5% $CO_2$), physiological medium (containing 117 mM NaCl, 4.7 mM KCl, 11.5 mM glucose, 1.2 mM $MgCl_2$, 10 μM pargyline, 1 mM ascorbate, 1.2 mM $NaH_2PO_4$ and 25 mM $NaHCO_3$, adjusted to pH 7.4). The slices were then washed with 0.9% NaCl and incubated in physiological medium with 0.1 μM [$^3$H] norepinephrine (30 minutes, 37° C.). The slices were again washed with 0.9% NaCl and then placed in tubes (borosilicate glass, 12×75 mm) containing 0.5 ml $Mg^{+2}$-free physiological medium with 50 μM corticosterone and 10 μM desipramine added to minimize norepinephrine reuptake. Samples were analyzed for [$^3$H] content at 5 minute intervals. After 75 minutes, the inhibitor drug was added. Fifteen minutes later NMDA was added to a concentration of 150 μM. The amount of [$^3$H] released was measured by liquid scintillation spectroscopy. The amount of NMDA-induced [$^3$H] release in the presence of the inhibitor was compared to the amount of NMDA-induced [$^3$H] release in the absence of the inhibitor to obtain comparative data for percent inhibition calculations.

Hence, there is herewith provided a method for preventing convulsions and neurodegenerative disorders induced by overstimulation of excitatory amino acid receptors in brain or spinal cord, which comprises administering to a mammal suffering from such convulsions or degenerative disease states, an NMDA antagonist of the formula:

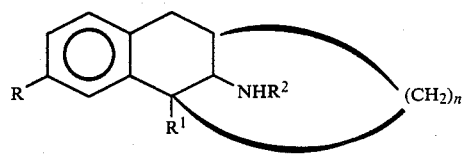

where
R is hydrogen, alkyl of 1 to 6 carbon atoms, alkoxy of 1 to 6 carbon atoms, hydroxy, alkanoyloxy of 2 to 6 carbon atoms, phenylalkoxy having 1 to 6 carbon atoms in the alkoxy moiety, halo or trifluoromethyl;

$R^1$ is alakyl of 1 to 6 carbon atoms, alkenyl of 2 to 6 carbon atoms or phenylalkyl having 1 to 6 carbon atoms in the alkyl moiety;

$R^2$ is hydrogen, alkyl of 1 to 6 carbon atoms, phenylalkyl having 1 to 6 carbon atoms in the alkyl moiety, alkenyl of 2 to 6 carbon atoms, alkynyl of 2 to 6 carbon atoms, thienylalkyl having 1 to 6 carbon atoms in the alkyl moiety or furylalkkyl having 1 to 6 carbon atoms in the alkyl moiety;

and n is one of the integers 2, 3, 4, 5 or 6;

or a pharmaceutically acceptable salt thereof.

To determine the effective amount of compound to be administered in alleviation of convulsions, the physician need only evaluate the effects of a given NMDA antagonist in the patient by incrementally increasing the oral dosage from about 50 mg/kg to about 1000 mg/kg until the desired anticonvulsant level is achieved. Similar techniques are followed by determining the effective dose range upon i.v. or i.m. administration. When using the compounds prophylactically to arrest declining cognitive function as in Altzheimer's dementia, a more subjective approach is taken such as by relating the drug dosage to improved memory responses or analogous desired responses which can be related to relief of overstimulation of the excitatory amino acid receptors. The effective dose range for such prophylactic treatments lie in the same range as for treatment of convulsions.

What is claimed is:

1. A process for preventing convulsions and neurodegenerative disorders induced by overstimulation of excitatory amino acid receptors, which comprises administering to a mammal suffering from such convulsions or neurodegenerative disorders, an anticonvulsant, neuroprotective amount of an NMDA antagonist of the formula:

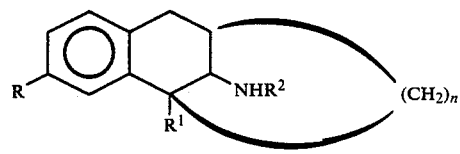

where
R is hydrogen, alkyl of 1 to 6 carbon atoms, alkoxy of 1 to 6 carbon atoms, hydroxy, alkanoyloxy of 2 to 6 carbon atoms, phenylalkoxy having 1 to 6 carbon atoms in the alkoxy moiety, halo or trifluoromethyl;

$R^1$ is alkyl of 1 to 6 carbon atoms, alkenyl of 2 to 6 carbon atoms or phenylalkyl having 1 to 6 carbon atoms in the alkyl moiety;

$R^2$ is hydrogen, alkyl of 1 to 6 carbon atoms, phenylalkyl having 1 to 6 carbon atoms in the alkyl moiety, alkenyl of 2 to 6 carbon atoms, alkynyl of 2 to 6 atoms, thienylalkyl having 1 to 6 carbon atoms in the alkyl moiety or furylalkyl having 1 to 6 carbon atoms in the alkyl moiety;

and n is one of the integers 2, 3, 4, 5 or 6;

or a pharmaceutically acceptable salt thereof.

2. A method for preventing brain cell damage resulting from overstimulation by excessive amounts of excitatory amino acids which comprises administering to a mammal suffering form neurodegeneration an effective amount of an NMDA antagonist of the formula:

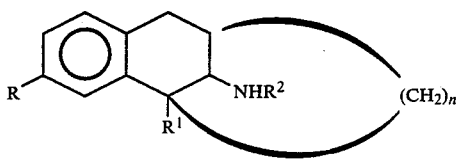

where

R is hydrogen, alkyl of 1 to 6 carbon atoms, alkoxy of 1 to 6 carbon atoms, hydroxy, alkanoyloxy of 2 to 6 carbon atoms, phenylalkoxy having 1 to 6 carbon atoms in the alkoxy moiety, halo or trifluoromethyl;

$R^1$ is alkyl of 1 to 6 carbon atoms, alkenyl of 2 to 6 carbon atoms or phenylalkyl having 1 to 6 carbon atoms in the alkyl moiety;

$R^2$ is hydrogen, alkyl of 1 to 6 carbon atoms, phenylalkyl having 1 to 6 carbon atoms in the alkyl moiety, alkenyl of 2 to 6 carbon atoms, alkynyl of 2 to 6 carbon atoms, thienylalkyl having 1 to 6 carbon atoms in the alkyl moiety or furylalkyl having 1 to 6 carbon atoms in the alkyl moiety;

and n is one of the integers 2, 3, 4, 5 or 6;

or a pharmaceutically acceptable salt thereof.

3. A process of claim 1 in which the NMDA antagonist is a compound of the formula:

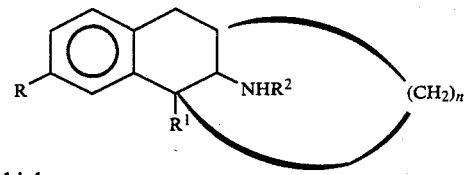

in which

R is hydroxy;

$R^1$ is methyl;

$R^2$ is methyl;

and n is 5;

or a pharmaceutically acceptable salt thereof.

4. A process of claim 1 in which the NMDA antagonist is N-(5,6,7,8,9,10,11,12-octahydro-3-methoxy-5-methyl-5,11-methanobenzocyclodecen-13-yl)-2-furanmethanamine.

5. A process of claim 1 in which the NMDA antagonist is N-(5,6,7,8,9,10,11,12-octahydro-3-methoxy-5-methyl-5,11-methanobenzocyclodecen-13-yl)-2-thiophenemethanamine.

6. A process of claim 1 in which the NMDA antagonist is (−)-13β-amino-5α-methyl-5,6,7,8,9,10,11,12-octahydro-5,11-methanobenzocyclodecen-3-ol.

7. A process of claim 1 in which the NMDA antagonists is (−)-13β-methylamino-3-methoxy-5-α-methyl-5,6,7,8,9,10,11,12-octahydro-5,11-methanobenzocyclodecene.

* * * * *